(12) United States Patent
Ding et al.

(10) Patent No.: US 9,434,665 B2
(45) Date of Patent: Sep. 6, 2016

(54) RUTHENIUM COMPLEX AND METHOD FOR PREPARING METHANOL AND DIOL

(71) Applicant: Shanghai Institute of Organic Chemistry, Chinese Academy of Sciences, Shanghai (CN)

(72) Inventors: Kuiling Ding, Shanghai (CN); Zhaobin Han, Shanghai (CN)

(73) Assignee: SHANGHAI INSTITUTE OF ORGANIC CHEMISTRY, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 14/436,842

(22) PCT Filed: Mar. 22, 2013

(86) PCT No.: PCT/CN2013/073095
§ 371 (c)(1),
(2) Date: Apr. 17, 2015

(87) PCT Pub. No.: WO2014/059757
PCT Pub. Date: Apr. 24, 2014

(65) Prior Publication Data
US 2016/0060195 A1    Mar. 3, 2016

(30) Foreign Application Priority Data

Oct. 19, 2012   (CN) .......................... 2012 1 0403332

(51) Int. Cl.
*C07C 29/136*    (2006.01)
*C07F 15/00*     (2006.01)
*B01J 31/24*     (2006.01)
*B01J 31/18*     (2006.01)
*C07F 19/00*     (2006.01)

(52) U.S. Cl.
CPC ............ *C07C 29/136* (2013.01); *B01J 31/189* (2013.01); *B01J 31/24* (2013.01); *B01J 31/2476* (2013.01); *C07F 15/0046* (2013.01); *C07F 19/00* (2013.01); *B01J 2231/643* (2013.01); *B01J 2531/0247* (2013.01); *B01J 2531/821* (2013.01)

(58) Field of Classification Search
CPC .............. C07F 15/0046; C07C 29/136; B01J 31/2476; B01J 31/24; B01J 31/189
USPC .............................. 556/21, 22; 568/861, 885
See application file for complete search history.

(56) References Cited

U.S. PATENT DOCUMENTS 8,124,816 B2    2/2012  Saudan et al.
2011/0237814 A1  9/2011  Kuriyama et al.

FOREIGN PATENT DOCUMENTS

CN    101142155 A    3/2008
CN    102177170 A    9/2011

OTHER PUBLICATIONS

International Search Report corresponding to PCT/CN2013/073095 mailed Aug. 1, 2013, 3 pages.

*Primary Examiner* — Porfirio Nazario Gonzalez
(74) *Attorney, Agent, or Firm* — Mintz, Levin, Cohn, Glovsky and Popeo, P.C.

(57) ABSTRACT

Provided is a method for preparing methanol and diol from cyclic carbonate, comprising: under a hydrogen atmosphere, in an organic solvent, and with the presence of a ruthenium complex (Ru(L)XYY') and an alkali, conducting a hydrogenation reduction reaction on the cyclic carbonate or polycarbonate to obtain methanol and diol. Also provided is a ruthenium complex prepared from ruthenium and a tridentate amido diphosphine ligand. Also provided is a deuterated methanol and deuterated diol preparation method by substituting the hydrogen and ruthenium complex with deuterium.

14 Claims, No Drawings

RUTHENIUM COMPLEX AND METHOD FOR PREPARING METHANOL AND DIOL

TECHNICAL FIELD

The present invention relates to the field of organic synthesis. In particular, the present invention relates to a method for preparing methanol and diol by using a ruthenium complex as catalyst.

BACKGROUND

Methanol is a simple, safe liquid oxygenous hydrocarbon fuel and can be easily stored and transported. Methanol is also an important chemical raw material which can be used to replace petroleum to synthesize a variety of products, such as methanol to olefins (MTO), methanol to propylene (MTP), methanol to aromatics (MTA) and so on. As an important energy carrier, methanol is an effective solution dealing with energy issues resulting from the depletion of petroleum, coal, natural gas in post oil-gas era [Olah, G. A., Geoppert, A. & Surya Prakash, G. K. *Beyond Oil and Gas. The Methanol Economy*, Wiley-VCH, 2006.]. In recent years, methanol production scale has increased rapidly (merely in China, 38 million tons of methanol was produced in 2010), however, such processes use coal, natural gas or petroleum as raw material, and, therefore, will face the challenge of depletion of fossil fuel resources, and such resources are difficult to regenerate.

On the other hand, diol compounds are fuel and industrial raw materials of significant uses. For example, 1,2-ethylene glycol is an extremely important chemical raw material and solvent, which can be widely used in polyester fibers, films, resins and engine coolants. Traditionally, 1,2-ethylene glycol is prepared by hydrolysis of ethylene oxide, however, a variety of produced byproducts directly affect the quality of the product. To address this issue, a new process called OMEGA was developed by Shell (UK), in which cyclic ethylene carbonate is firstly obtained from ethylene oxide and carbon dioxide, and 1,2-ethylene glycol is obtained by hydrolysis of the cyclic ethylene carbonate under a catalyst with emission of carbon dioxide [http://en.wikipedia.org/wiki/OMEGA_process#cite_note-0.]. 1,2-ethylene glycol can be obtained by OMEGA process at 99% selectivity, however, the deficiency for this process is that carbon dioxide can not be effectively utilized and released back to the environment upon reaction.

Carbon dioxide is a greenhouse gas affecting environment, however, carbon dioxide is also a inexhaustible, inexpensive, safe and renewable carbon resources [Carbon Dioxide as Chemical Feedstock, (Ed.: M. Aresta), Wiley-VCH, Weinheim, 2010)]. Catalytic hydrogenation of carbon dioxide to produce methanol is an important passway to realize methanol economy. This reaction is thermodynamically feasible, however, carbon dioxide is generally very difficult to be directly reduced, which is the main challenge in the industry and academia, due to the high inertia of carbon-oxygen double bond. At present, a few heterogeneous catalyst systems have been reported for this reaction, however, a prevalent defect in it is that the reaction should be performed under strict conditions, such as high temperature and high pressure (250° C., 50 atm), and the efficiency and selectivity of the reaction are not high enough [W. Wang, S. P. Wang, X. B. Ma, J. L. Gong, Chem. Soc. Rev. 2011, 40, 3703-3727]. On the other hand, currently only two cases were reported, which refer to the direct hydrogenation of carbon dioxide into methanol by using a homogeneous catalyst system and hydrogen as a hydrogen source, however, the catalytic efficiency of the two methods is relatively low (the highest conversion number for catalyst is ≤221) [C. A. Huff, M. S. Sanford, *J. Am. Chem. Soc.* 2011, 133, 18122-18125], [S. Wesselbaum, T. vom Stein, J. Klankermayer, W. Leitner, *Angew. Chem., Int. Ed.* 2012, 51, 7499-7502]. So far, there is no practical catalytic process for catalytically hydrogenating carbon dioxide into methanol. On the other hand, in 2011, Milstein et al., reported a method for hydrogenating dimethyl carbonate to synthesize methanol by using ruthenium complex as homogeneous catalyst [E. Balaraman, C. Gunanathan, J. Zhang, L. J. W. Shimon, D. Milstein, *Nature Chem.* 2011, 3, 609-614]. In the prior art, dimethyl carbonate is obtained through transesterification between cyclic ethylene carbonate and methanol (Aresta, M. (ed.) *Carbon Dioxide as Chemical Feedstock* (Wiley-VCH, 2010). However, the market price of dimethyl carbonate is significantly higher than that of methanol, so that such catalytic system obviously has no practicability and economic value. Moreover, it is well-known to a person skilled in the art that the structure of used ligand will greatly affect catalytic activity of the resulting complex, when using a metal complex as catalyst; in other words, small changes in the structure of ligand will result in the loss of catalytic activity of the resulting metal complex.

Summing up, there is an urgent need in the art for a method to directly or indirectly convert carbon dioxide into methanol under mild conditions, and such method not only has a high conversion efficiency, but also has excellent economy. Additionally, in the prior art, degradation of polycarbonate materials relys on hydrolysis, the degradation products are diol and carbon dioxide, wherein carbon dioxide will release back into environment again. Therefore, there is an urgent need in the art for a method to degrade polycarbonate through hydrogenation and reduction under mild conditions.

SUMMARY OF THE INVENTION

One object of the present invention is to provide a method for preparing methanol and diol by using cyclic carbonate, and a method for the degradation of polycarbonate through hydrogenation and reduction under mild conditions.

In the first aspect, the present invention provides a method for preparing methanol and diol, said method comprising: under hydrogen atmosphere, subjecting a cyclic carbonate or polycarbonate to the following reaction under the action of a catalyst, so as to give methanol and diol,

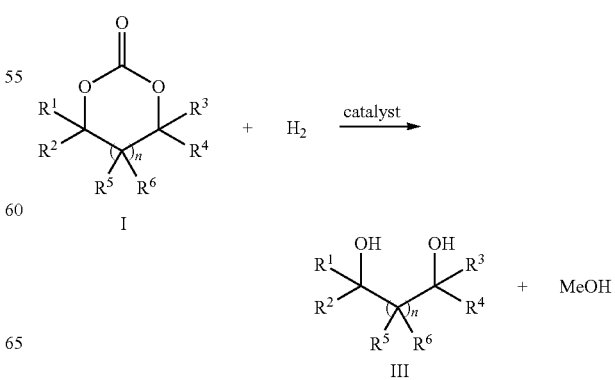

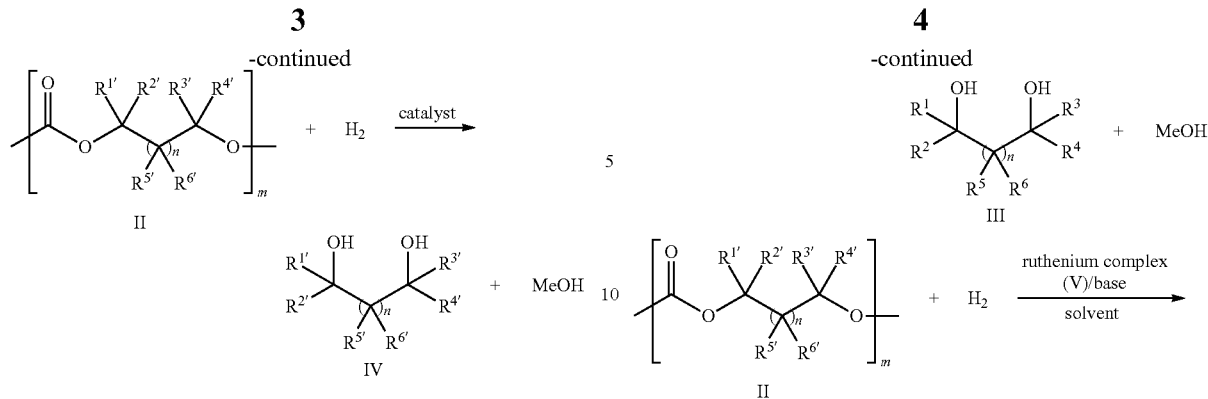

in formula I and III:

n=0~20, m=2~1000000;

$R^1$, $R^2$, $R^3$, $R^4$, $R^5$, $R^6$ can be independently selected from a hydrogen, a $C_1$~$C_{20}$ alkyl, a $C_4$~$C_{24}$ aryl, a $C_5$~$C_{25}$ aryl alkyl, —$(C_1$~$C_8)$—$OR^7$, —$(C_1$~$C_8)$—$SR^8$, or —$(C_1$~$C_8)$—$NR^9R^{10}$;

$R^5$, $R^6$ may be further independently selected from a $C_4$~$C_{10}$ cycloalkyl;

wherein $R^7$, $R^8$, $R^9$, $R^{10}$ are independently selected from a $C_1$~$C_{10}$ alkyl, a $C_4$~$C_{24}$ aryl or a $C_5$~$C_{25}$ aryl alkyl, and $R^9$, $R^{10}$ may also be joined to form a cyclic amine group with the nitrogen atom;

when n=0, $R^1$ and $R^3$ may be joined to form an alicyclic group or aryl ring;

when n≥1, $R^1$ and $R^5$, $R^3$ and $R^6$ may be joined to form an alicyclic group or an aryl ring;

in formula II and IV:

$R^{1'}$, $R^{2'}$, $R^{3'}$, $R^{4'}$, $R^{5'}$, $R^{6'}$ may be independently selected from a hydrogen, a $C_1$~$C_{20}$ alkyl, a $C_4$~$C_{24}$ aryl, a $C_5$~$C_{25}$ aryl alkyl, —$(C_1$~$C_8)$—$OR^{7'}$, —$(C_1$~$C_8)$—$SR^{8'}$ or —$(C_1$~$C_8)$—$NR^{9'}R^{10'}$;

$R^{5'}$, $R^{6'}$ may be further independently selected from a $C_4$~$C_{10}$ cycloalkyl;

wherein $R^{7'}$, $R^{8'}$, $R^{9'}$, $R^{10'}$ are independently selected from a $C_1$~$C_{10}$ alkyl, a $C_4$~$C_{24}$ aryl or a $C_5$~$C_{25}$ aryl alkyl, $R^{9'}$, $R^{10'}$ may be further joined to form a cyclic amine group with the nitrogen atom;

when n=0, $R^{1'}$ and $R^{3'}$ may be joined to form an alicyclic group or aryl ring;

when n≥1, $R^{1'}$ and $R^{5'}$, $R^{3'}$ and $R^{6'}$ may be joined to form an alicyclic group or an aryl ring.

In a preferred embodiment, the catalyst is a compound of transition metal of Group VIIIB.

In a preferred embodiment, the transition metal of Group VIIIB is selected from Fe, Co, Ni, Ru, Rh, Pd, Os, Ir or Pt.

In another preferred embodiment, the method includes conducting the following reaction in the presence of an organic solvent and a base:

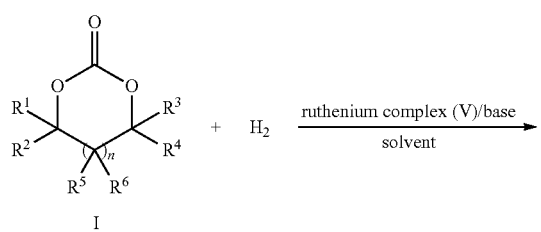

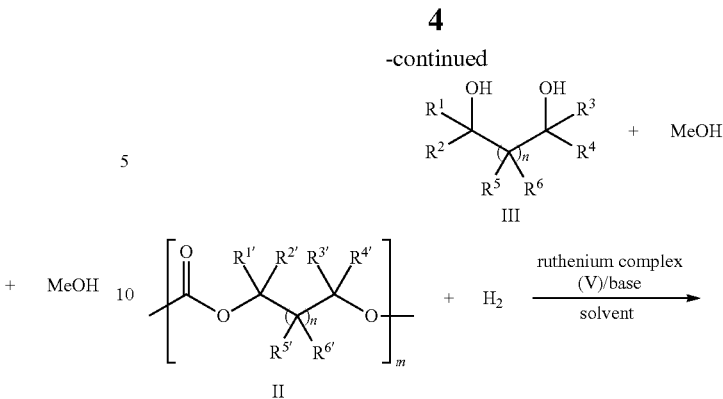

wherein the compounds of structural formula I, II, III and IV are defined as in claim 1, and the ruthenium complex V has the general structural formula V:

$$Ru(L)XYY' \qquad (V);$$

in formula V:

X is carbon monoxide, triphenylphosphine, pyridine, tetrahydrofuran or dimethyl sulfoxide;

Y, Y' are independently selected from: a hydride ion, a hydroxyl ion, a chloride ion, a bromide ion, an iodide ion and $BH_4^-$, $BH_3CN^-$, $BH(Et)_3^-$, $BH(sec\text{-}Bu)_3^-$, $AlH_4^-$ or $AlH_2(OCH_2CH_2CH_3)_2^-$;

wherein L is a tridentate amino bisphosphorus ligand of general structural formula VI:

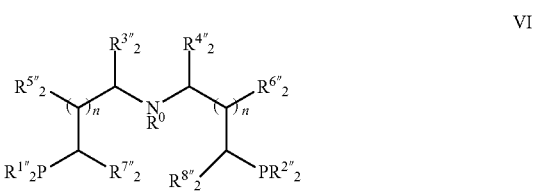

in general formula VI, n=0~3;

$R^0$ is H;

$R^{1''}$, $R^{2''}$ are independently selected from a $C_1$~$C_{10}$ alkyl, a $C_3$~$C_{10}$ cycloalkyl, a $C_4$~$C_{24}$ aryl or an adamantyl, wherein the aryl includes an unsubstituted or substituted aryl;

$R^{3''}$, $R^{4''}$, $R^{5''}$, $R^{6''}$, $R^{7''}$, $R^{8''}$ are independently selected from a hydrogen, a $C_1$~$C_{10}$ alkyl, a $C_3$~$C_{10}$ cycloalkyl, a $C_1$~$C_{10}$ alkoxy or a $C_4$~$C_{36}$ aryl;

when n=0, $R^{3''}$ and $R^{7''}$, $R^{4''}$ and $R^{8''}$ may be joined to form an alicyclic group or an aryl ring;

when n≥1, $R^{3''}$ and $R^{5''}$, $R^{4''}$ and $R^{6''}$, $R^{5''}$ and $R^{7''}$ as well as $R^{6''}$ and $R^{8''}$ may be joined to form an alicyclic group or an aryl ring.

In a further preferred embodiment, the ruthenium complex V is shown in structural formula 1a:

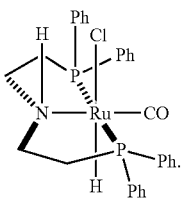

1a

In other preferred embodiments, the ruthenium complex is shown in structural formula 1b-1e:

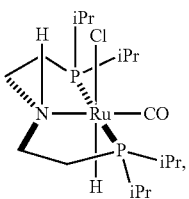

1b

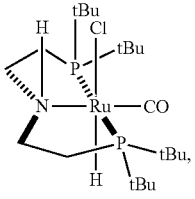

1c

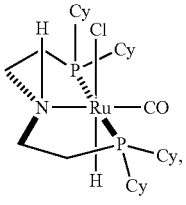

1d

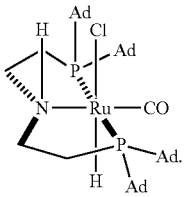

1e

In a specific embodiment, the molar ratio of the cyclic carbonate or polycarbonate to ruthenium complex is 100~1000000:1.

In a preferred embodiment, the molar ratio of the cyclic carbonate or polycarbonate to ruthenium complex is 1000~100000; preferably, 10000~100000.

In a specific embodiment, the base is an alkali metal salt of alcohol, an alkali metal carbonate, or an alkali metal hydroxide.

In a preferred embodiment, said base is potassium tert-butoxide, sodium tert-butoxide, potassium isopropoxide, sodium isopropoxide, sodium ethoxide, or potassium carbonate, sodium carbonate, sodium hydroxide or potassium hydroxide.

In a further preferred embodiment, said base is potassium tert-butoxide.

In a specific embodiment, the ruthenium complex catalyzes the hydrogenation of cyclic carbonate under neutral conditions to give methanol and corresponding diol.

In a specific embodiment, the molar ratio of base to ruthenium complex is 1 to 100:1.

In a preferred embodiment, the molar ratio of base to ruthenium complex is 1 to 20:1, more preferably 1-5:1.

In a further preferred embodiment, the molar ratio of base to ruthenium complex is 1:1.

In a specific embodiment, the temperature for the reaction is 60-180° C.

In a preferred embodiment, the temperature for the reaction is 80-150° C., more preferably, 80-140° C.

In a specific embodiment, the reaction time for the reaction is 0.1-1000 hours.

In a preferred embodiment, the reaction time for the reaction is 0.5-100 hours, more preferably, 1-72 hours.

In a specific embodiment, the hydrogen pressure for the reaction is 1-100 atmospheres.

In a preferred embodiment, the hydrogen pressure for the reaction is 5-60 atmospheres, more preferably 50 atmospheres.

In a preferred embodiment, the inert solvent is tetrahydrofuran, 2-methyl tetrahydrofuran, dioxane, ethylene glycol dimethyl ether, tert-butyl methyl ether, benzene, toluene, xylene, methanol, ethanol, isopropanol, t-butanol.

In a further preferred embodiment, the organic solvent is tetrahydrofuran, dioxane, or toluene.

In the second aspect, a ruthenium complex of formula V is provided in the present invention, $$Ru(L)XYY' \quad (V);$$

in formula V:

X is carbon monoxide, triphenylphosphine, pyridine, tetrahydrofuran or dimethyl sulfoxide;

Y, Y' are independently selected from: a hydride ion, a hydroxyl ion, a chloride ion, a bromide ion, an iodide ion and $BH_4^-$, $BH_3CN^-$, $BH(Et)_3^-$, $BH(sec-Bu)_3^-$, $AlH_4^-$ or $AlH_2(OCH_2CH_2CH_3)_2^-$;

wherein L is a tridentate amino bisphosphorus ligand of structural formula VI:

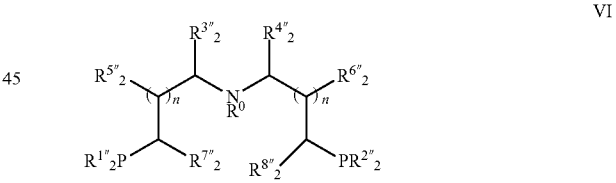

VI in general formula VI, n=0~3;

$R^0$ is H;

$R^{1'''}$, $R^{2'''}$ are independently selected from a $C_1$~$C_{10}$ alkyl, a $C_3$~$C_{10}$ cycloalkyl, a $C_4$~$C_{24}$ aryl or an adamantyl, wherein the aryl is an unsubstituted or substituted aryl;

$R^{3'''}$, $R^{4'''}$, $R^{5'''}$, $R^{6'''}$, $R^{7'''}$, $R^{8'''}$ are independently selected from a hydrogen, a $C_1$~$C_{10}$ alkyl, a $C_3$~$C_{10}$ cycloalkyl, a $C_1$~$C_{10}$ alkoxy or a $C_4$~$C_{36}$ aryl;

when n=0, $R^{3'''}$ and $R^{7'''}$, $R^{4'''}$ and $R^{8'''}$ may be joined to form an alicyclic group or an aryl ring;

when n≥1, $R^{3'''}$ and $R^{5'''}$, $R^{4'''}$ and $R^{6'''}$, $R^{5'''}$ and $R^{7'''}$ as well as $R^{6'''}$ and $R^{8'''}$ may be joined to form an alicyclic group or an aryl ring;

wherein, when all of $R^{3'''}$, $R^{4'''}$, $R^{5'''}$, $R^{6'''}$, $R^{7''''}$ and $R^{8''''}$ is H, $R^{2''''}$ is not a phenyl.

In a specific embodiment, the ruthenium complex is shown in structural formula 1b-1e:

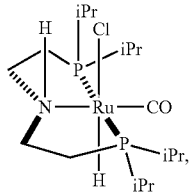
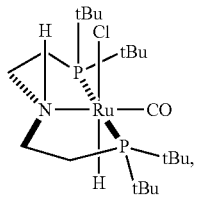
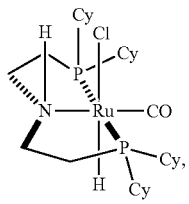
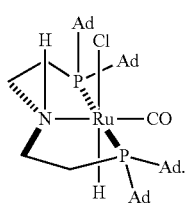

In a preferred embodiment, the ruthenium complex is used to reduce carbonate through hydrogenation.

In a further preferred embodiment, the ruthenium complex is used to reduce cyclic carbonate or polycarbonate through hydrogenation to produce methanol and diol.

In the third aspect, a method for preparing deuterated methanol and deuterated diol is provided in the present invention, and the method includes performing the method according to the second aspect of the present invention by using deuterium $D_2$ instead of hydrogen $H_2$, so as to give deuterated methanol and deuterated diol.

In the fourth aspect, a method for preparing alcohol is provided in the present invention, and the method includes, in the presence of a ruthenium complex (V) and a base, reducing carbonate through hydrogenation in a organic solvent, so as to give alcohol, wherein the ruthenium complex is shown in formula V $$Ru(L)XYY' \qquad (V);$$

in formula V:

X is carbon monoxide, triphenylphosphine, pyridine, tetrahydrofuran or dimethyl sulfoxide;

Y, Y' are independently selected from: a hydride ion, a hydroxyl ion, a chloride ion, a bromide ion, an iodide ion and $BH_4^-$, $BH_3CN^-$, $BH(Et)_3^-$, $BH(sec-Bu)_3^-$, $AlH_4^-$ or $AlH_2(OCH_2CH_2CH_3)_2^-$;

wherein L is a tridentate amino bisphosphorus ligand of general structural formula VI:

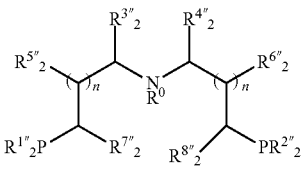

in general formula VI, n=0~3;

$R^0$ is H;

$R^{1''}$, $R^{2''}$ are independently selected from a $C_1$~$C_{10}$ alkyl, a $C_3$~$C_{10}$ cycloalkyl, a $C_4$~$C_{24}$ aryl or an adamantyl, wherein the aryl is an unsubstituted or substituted aryl;

$R^{3''}$, $R^{4''}$, $R^{5''}$, $R^{6''}$, $R^{7''}$, $R^{8''}$ are independently selected from a hydrogen, a $C_1$~$C_{10}$ alkyl, a $C_3$~$C_{10}$ cycloalkyl, a $C_1$~$C_{10}$ alkoxy or a $C_4$~$C_{36}$ aryl;

when n=0, $R^{3''}$ and $R^{7''}$, $R^{4''}$ and $R^{8''}$ may be joined to form an alicyclic group or an aryl ring;

when n≥1, $R^{3''}$ and $R^{5''}$, $R^{4''}$ and $R^{6''}$, $R^{5''}$ and $R^{7''}$ as well as $R^{6''}$ and $R^{8''}$ may be joined to form an alicyclic group or an aryl ring.

It should be understood that in the present invention, the technical features specifically above and below (such as the Examples) can be combined with each other, thereby constituting a new or preferred technical solution which needs not be individually described.

DETAILED DESCRIPTION OF THE INVENTION

Through comprehensive and intensive research, the inventors unexpectedly found that by using a complex formed from ruthenium and tridentate amino bisphosphorus PNP pincer-like ligand as a catalyst and hydrogen gas as hydrogen source, cyclic carbonate can be reduced through hydrogenation, so as to obtain methanol and 1,2-ethylene glycol and derivatives thereof with high efficiency and selectivity and indirectly achieve the chemical conversion from carbon dioxide to methanol. For the first time, the inventors have also found that using the catalyst of the invention, polycarbonate can be efficiently degraded to methanol and diol through catalytic hydrogenation, thereby recovering diol and methanol from polycarbonate waste. Furthermore, the inventors found that catalysts of the invention can be used to efficiently catalyze the reduction of cyclic carbonate through deuteration, so as to prepare deuterated methanol and deuterated diol. Based on the above, the present invention is completed.

Definition of Groups

In the present invention, "$C_1$~$C_{10}$ alkyl" means a straight or branched chain alkyl having up to 10 carbon atoms, such as methyl, ethyl, propyl, isopropyl, butyl, isobutyl, tert-butyl, pentyl, isopentyl, neopentyl, hexyl, t-hexyl, heptyl, iso-heptyl, octyl and iso-octyl. Similarly, "$C_1$~$C_{10}$ alkoxy" means alkyl as defined above attached via an oxygen atom, such as methoxy, ethoxy, propoxy, butoxy and the like.

In the present invention, "aryl" means substituents with properties of aromatic ring structure, such as phenyl, furyl, thienyl, pyridyl, quinolyl, indolyl. In the present invention, aryl includes unsubstituted or substituted aryl, wherein "substituted" refers to having one or more substituents. Representative substituents include, but are not limited to: the above-described alkyl, alkoxy and a halogen and nitro group. Representative aryl includes an aryl with electron-donating and/or electron-withdrawing substituent, such as p-tolyl, p-methoxyphenyl, p-chlorophenyl, and the like. Similarly, "arylalkyl" means a substituent formed by connecting aryl and alkyl, such as phenylmethyl, phenylethyl, phenylpropyl, and the like.

Diol

As used herein, the term "diol" can be interchangeably used with the term "dihydroxy compound", which refers to a compound having two hydroxyls at the end. A person skilled in the art will understand that, in a specific embodiment, the term may include compounds such as alcohol, phenol, depending on the particular group connected with the hydroxyl.

In other embodiments, in addition to two hydroxyls at the end (which can be formed by the catalytic cracking process of the present invention), the "diol" of the present invention can optionally contain hydroxyl(s) at other position(s).

Conversion Efficiency

As used herein, the term "conversion efficiency" (or efficiency rate) is the percent of the amount of reactants consumed during a chemical reaction in the total amount of initially added reactants. For the reaction of the present invention, in the case of hydrogenation reaction of cyclic carbonate, the conversion efficiency means that, under certain conditions and within certain reaction time, the mole ratio of the consumed cyclic carbonate to the initially added cyclic carbonate, expressed as a percentage.

Conversion Number

As used herein, the term "conversion number" refers to the mole ratio of the converted reactants to catalyst, within a given period of time. In the reaction of the present invention, in the case of hydrogenation reaction of cyclic carbonate, the conversion number means that, under certain conditions and within certain reaction time, the mole ratio of the consumed cyclic carbonate to the catalyst.

In the reaction of the present invention, the conversion rate and the conversion number can be calculated by determining carbonate through gas chromatography with p-xylene as an internal standard and standard curve method; that is, p-xylene is used as an internal standard, and standard curve is plotted according to the ratio of the peak area of carbonate, methanol and diol on gas chromatogram to the peak area of xylene. The content of carbonate, methanol and diol in a reaction system can be determined by determining the proportion of peak areas in the reaction system.

Carbonate

As used herein, the term "carbonate" includes straight-chain carbonate (i.e., non-cyclic, non-polymeric carbonates, such as dimethyl carbonate), cyclic carbonate, polycarbonate. In particular, the cyclic carbonate and polycarbonate of the present invention are shown in formula I and II, respectively:

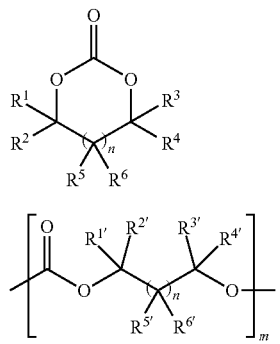

I

II in formula I:
n=0~20, m=2~1000000;
$R^1$, $R^2$, $R^3$, $R^4$, $R^5$, $R^6$ can independently be a hydrogen, a $C_1$~$C_{20}$ alkyl, a $C_4$~$C_{24}$ aryl, a $C_5$~$C_{25}$ aryl alkyl, —($C_1$~$C_8$)—$OR^7$, —($C_1$~$C_8$)—$SR^8$, or —($C_1$~$C_8$)—$NR^9R^{10}$;
$R^5$, $R^6$ may independently be a $C_4$~$C_{10}$ cycloalkyl;
$R^7$, $R^8$, $R^9$, $R^{10}$ are independently selected from a $C_1$-$C_{10}$ alkyl, a $C_4$~$C_{24}$ aryl or a $C_5$-$C_{25}$ aryl alkyl;
$R^9$, $R^{10}$ may also be joined to form a cyclic amine group with the nitrogen atom;
when n=0, $R^1$ and $R^3$ may be joined to form an alicyclic group or aryl ring;
when n≥1, $R^1$ and $R^5$, $R^3$ and $R^6$ may be joined to form an alicyclic group or an aryl ring;
in formula II:
$R^1$, $R^{2'}$, $R^{3'}$, $R^{4'}$, $R^{5'}$, $R^{6'}$ may be independently selected from a hydrogen, a $C_1$~$C_{20}$ alkyl, a $C_4$~$C_{24}$ aryl, a $C_5$~$C_{25}$ aryl alkyl, —($C_1$~$C_8$)—$OR^7$, —($C_1$~$C_8$)—$SR^8$ or —($C_1$~$C_8$)—$NR^9R^{10}$;
$R^{5'}$, $R^{6'}$ may be independently further selected from a $C_4$~$C_{10}$ cycloalkyl;
wherein $R^{7'}$, $R^{8'}$, $R^{9'}$, $R^{10'}$ are independently selected from a $C_1$~$C_{10}$ alkyl, a $C_4$~$C_{24}$ aryl or a $C_5$~$C_{25}$ aryl alkyl, $R^{9'}$, $R^{10'}$ may be further joined to form a cyclic amine group with the nitrogen atom;
when n=0, $R^{1'}$ and $R^{3'}$ may be joined to form an alicyclic group or aryl ring; when n≥1, $R^{1'}$ and $R^{5'}$, $R^{3'}$ and $R^{6'}$ may be joined to form an alicyclic group or an aryl ring.

A person skilled in the art will know that cyclic carbonate is an important class of industrial chemical and solvent, which can be produced in large-scale through the reaction of carbon dioxide and epoxy compound. For example, industrialization of the process for preparation of ethylene carbonate from carbon dioxide and ethylene oxide has been achieved. Catalytic hydrogenation of cyclic carbonate has significant practical value, since carbon dioxide can be efficiently and indirectly used and important fuels and industrial raw materials, such as methanol and 1,2-ethylene glycol can be obtained.

Catalyst of the Present Invention

The catalyst of the invention is a ruthenium complex of general structural formula V. The ruthenium complex comprises tridentate amino bisphosphorus ligand L of general structural formula VI.

Ru(L)XYY' (V)

in general formula V:
X is independently selected from carbon monoxide, triphenylphosphine, pyridine, tetrahydrofuran or dimethyl sulfoxide.
Y, Y' are independently selected from: a hydride ion, a hydroxyl ion, a chloride ion, a bromide ion, an iodide ion and $BH_4^-$, $BH_3CN^-$, $BH(Et)_3^-$, $BH(sec-Bu)_3^-$, $AlH_4^-$ or $AlH_2(OCH_2CH_2CH_3)_2^-$. Y and Y' may be identical or different from each other.

Tridentate amino bisphosphorus ligand L comprised in general formula V is represented by general structural formula VI:

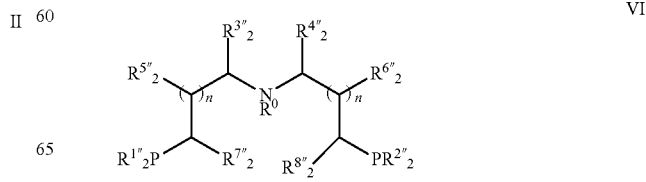

VI in general formula VI, n=0~3;
R⁰ is H;
$R^{1''}$, $R^{2''}$ are independently selected from a $C_1$~$C_{10}$ alkyl, a $C_3$~$C_{10}$ cycloalkyl, a $C_4$~$C_{24}$ aryl or an adamantyl;
$R^{3''}$, $R^{4''}$, $R^{5''}$, $R^{6''}$, $R^{7''}$, $R^{8''}$ are independently selected from a hydrogen, a $C_1$~$C_{10}$ alkyl, a $C_3$~$C_{10}$ cycloalkyl, a $C_1$~$C_{10}$ alkoxy or a $C_4$~$C_{36}$ aryl;
when n=0, $R^{3''}$ and $R^{7''}$, $R^{4''}$ and $R^{8''}$ may be joined to form an alicyclic group or an aryl ring;
when n≥1, $R^{3''}$ and $R^{5''}$, $R^{4''}$ and $R^{6''}$, $R^{5''}$ and $R^{7''}$ as well as $R^{6''}$ and $R^{8''}$ may be joined to form an alicyclic group or an aryl ring.

In a specific embodiment, the catalyst of the invention, i.e., ruthenium complex is shown in the following structural formula 1a-1e:

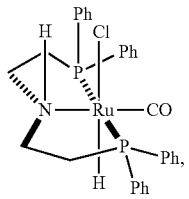

1a

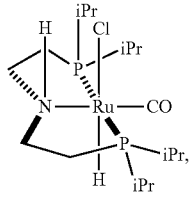

1b

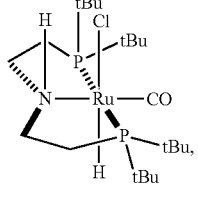

1c

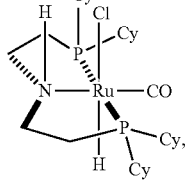

1d

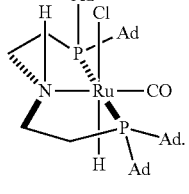

1e

Preparation Method for the Catalyst of the Invention

The Ruthenium catalysts of the present invention can be prepared by the following method:

Under an inert gas, such as nitrogen or argon atmosphere, at 60~120° C., 1 equivalent of ruthenium metal precursor, e.g., [RuHCl(CO)(PPh₃)₃], [RuH₂(CO)(PPh₃)₃], RuCl₂(PPh₃)₃, [RuCl₂(C₆H₆)]₂, [RuHCl(PPh₃)₃], Ru(DMSO)₄Cl₂, [Ru(cod)Cl₂], [Ru(nbd)Cl₂] reacts with 1 to 1.2 equivalents of tridentate amino bisphosphorus ligand in a solvent for 0.5-20 hrs to obtain the catalyst. Wherein DMSO represents dimethylsulfoxide, cod represents 1,5-cyclooctadiene, nbd represents norbornadiene.

Use of the Catalyst of the Invention

The catalyst of the invention, i.e., ruthenium complex, can be used under mild conditions to reduce carbonates, including cyclic carbonate, polycarbonate and linear carbonate through hydrogenation into methanol or other corresponding alcohols or diol, thereby indirectly converting carbon dioxide into methanol, and giving corresponding diol. Reducing carbonate through hydrogenation by using the ruthenium complex of the present invention will possess high conversion efficiency, excellent economy and convenience of operation.

Method for Preparing Methanol and Diol of the Present Invention

The present invention provides a novel method for preparing methanol and 1,2-ethylene glycol as well as other diol derivatives through catalytic hydrogenation. In the method of the present invention, for reducing cyclic carbonate or polycarbonate through hydrogenation, the ruthenium complex formed with a ligand is used as a catalyst, and hydrogen gas is used as hydrogen source, thereby obtaining methanol and 1,2-ethylene glycol and derivatives thereof with high efficiency and high selectivity.

In a specific embodiment, the method of the present invention includes: under a hydrogen atmosphere, in an organic solvent, in the presence of a ruthenium complex (V) and a base, reducing cyclic carbonate (General Formula I) or polycarbonate (General Formula II) through the following hydrogenation reaction, thereby obtaining methanol and corresponding diol III or IV,

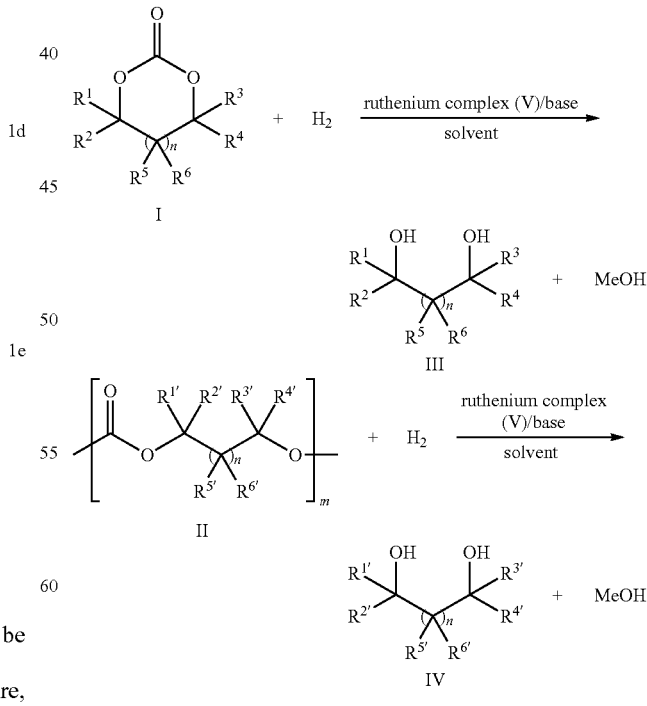

Each substituent and ruthenium complex as shown in the above reaction scheme are defined as above.

In a specific embodiment, the ruthenium complex of the following structural formula 1a-1e is used in the above reaction:

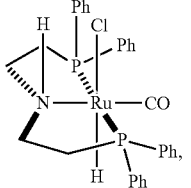
1a

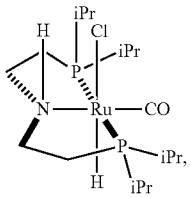
1b

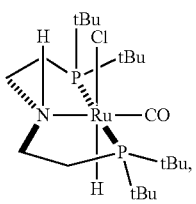
1c

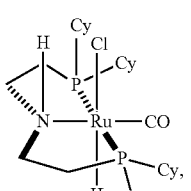
1d

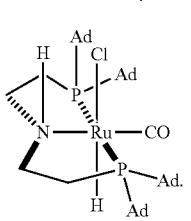
1e

The base can be used in the method of the invention includes an alkali metal salt of alcohol, such as potassium tert-butoxide, sodium tert-butoxide, potassium isopropoxide, sodium isopropoxide, sodium ethoxide; an alkali metal carbonate, such as potassium carbonate, sodium carbonate; an alkali metal hydroxide, such as sodium hydroxide or potassium hydroxide. In a preferred embodiment, an alkali metal salt of alcohol is used as a base; and preferably, potassium tert-butoxide is used as the base.

In a specific embodiment, the molar ratio of the cyclic carbonate or polycarbonate to ruthenium complex is 100~1000000:1. In a preferred embodiment, the molar ratio of the cyclic carbonate or polycarbonate to ruthenium complex is 1000~100000; preferably, 10000~100000, 1000~100000.

In a specific embodiment, the molar ratio of the base to the ruthenium complex is 1 to 100:1. In a preferred embodiment, the molar ratio of the base to the ruthenium complex is 1 to 20:1, more preferably 1-5:1. In a further preferred embodiment, the molar ratio of the base to the ruthenium complex is 1:1.

In a specific embodiment, the temperature for the reaction is 60-180° C. In a preferred embodiment, the temperature for the reaction is 80-150° C., more preferably, 80-140° C.

In a specific embodiment, the reaction time for the reaction is 0.1-1000 hours. In a preferred embodiment, the reaction time for the reaction is 0.5-100 hours, more preferably, 1-72 hours.

In a specific embodiment, the hydrogen pressure for the reaction is 1-100 atmospheres. In a preferred embodiment, the hydrogen pressure for the reaction is 5-60 atmospheres, more preferably 10-50 atmospheres.

The organic solvent can be used in the method of the invention includes tetrahydrofuran, 2-methyl tetrahydrofuran, dioxane, ethylene glycol dimethyl ether, tert-butyl methyl ether, benzene, toluene, xylene, methanol, ethanol, isopropanol, t-butanol, etc. In a preferred embodiment, ethers, such as tetrahydrofuran, dioxane, or toluene can be used in the method of the invention.

Moreover, according to the teachings of the present invention and the prior art, a person skilled in the art will readily appreciate that methanol and other monohydric alcohols can be prepared by using linear carbonate, i.e., non-cyclic, non-polymeric carbonate as raw material for the hydrogenation reaction.

Preparation Method of the Present Invention for Deuterated Methanol and Deuterated Diol According to the method of the invention for preparing methanol and diol, the inventors also use deuterium instead of hydrogen to reduce cyclic carbonate, thereby producing deuterated methanol and deuterated diol.

Moreover, by using cyclic carbonate, polycarbonate or routine carbonate, a person skilled in the art can prepare other deuterated monohydric alcohols with flexibility.

Main Advantages of the Present Invention

1. The cyclic carbonate can be conveniently prepared in large-scale industrialization from reacting an epoxy compound with carbon dioxide, therefore, the method of the invention is capable of generating methanol and diol from cyclic carbonate through catalytic hydrogenation, thereby achieving the purpose of the invention, that is, indirectly converting carbon dioxide into methanol, and the resulting diol is extremely valuable fuel and chemical raw material;

2. Methanol and diol can be produced from waste of polycarbonate with high efficiency and high selectivity through catalytic hydrogenation by using the method of the present invention, and compared with hydrolysis of polycarbonate, the method of the present invention will have higher atom economy;

3. No waste is produced according to the method of the present invention, which meets the technical requirements for environmentally sustainable economic development;

4. The method of the present invention is simple, and can be carried out under mild conditions with low cost;

5. The method of the present invention may also be used to prepare deuterated methanol and deuterated diol.

The present invention will be illustrated in the following referring to the specific examples; however, the present invention is not limited to such examples. For the experimental methods in the following examples the specific conditions of which are not specifically indicated, they are performed under routine conditions or manufacturer's instruction. All the percentages or fractions refer to weight percentage and weight fraction, unless stated otherwise.

EXAMPLE 1

Preparation of Catalyst Ruthenium Complex 1a

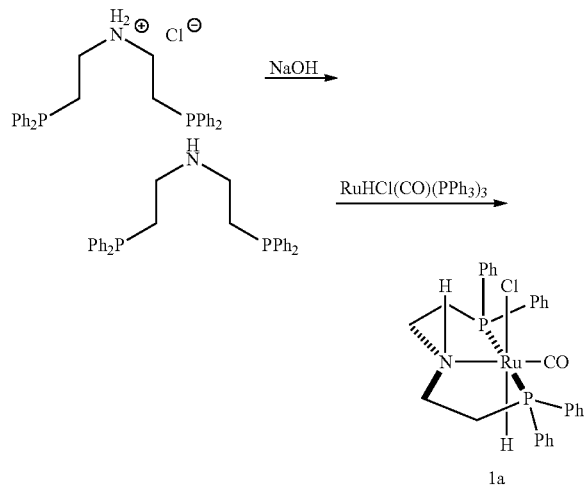

Under an inert gas such as nitrogen or argon atmosphere, into a 100 mL Schlenk tube was added HCl.HN(CH$_2$CH$_2$PPh$_2$)$_2$ (1.20 g, 2.51 mmol), toluene (20 mL) and 15% aqueous sodium hydroxide (10 mL). The reaction mixture was stirred at room temperature until the solid was completely dissolved. The organic phase was separated under an inert atmosphere, and washed twice with distilled water (2×5 mL). The combined aqueous phase was extracted twice with toluene (2×10 mL). All of the organic phases were combined and dried over anhydrous sodium sulfate. The drying agent was removed by filtration, and the solvent was removed under reduced pressure in vacuo to give a crude product of free amino bisphosphorus ligand. The crude product was dissolved in toluene (18 mL), RuHCl(CO)(PPh$_3$)$_3$ (2.28 g, 2.39 mmol) was added, and refluxed for 2 hours. The reaction system was cooled to room temperature, and hexane (10 mL) was added. Precipitates were filtered, and washed with hexane. The precipitates were dried in vacuo to give ruthenium complex 1a (1.42 g, 97% yield).

$^1$H NMR (400 MHz, CDCl$_3$) δ 7.80-7.70 (m, 8H), 7.52-7.16 (m, 12H), 4.36 (br s, 1H), 3.38-3.25 (m, 2H), 2.82-2.76 (m, 2H), 2.45-2.35 (m, 4H), −15.41 (t, J=19.6 Hz, 1H) ppm; $^{31}$P NMR (161.9 MHz, CDCl$_3$) δ 52.6 (d, J=18.1 Hz) ppm; HRMS (MALDI) m/z calcd. for C$_{29}$H$_{28}$NOP$_2$$^{96}$Ru: 564.0717. Found: 564.0699 [M-H$_2$—Cl]$^+$, IR (film) 1972, 1904 cm$^{-1}$.)

EXAMPLE 2

Preparation of Catalyst Ruthenium Complex 1b

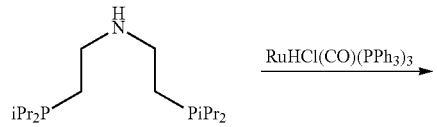

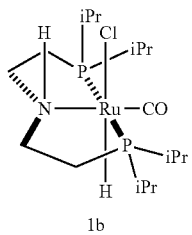

HN(CH$_2$CH$_2$P$^i$Pr$_2$)$_2$ (217 mg, 0.710 mmol) and RuHCl(CO)(PPh$_3$)$_3$ (644 mg, 0.676 mmol) were dissolved in toluene (4 mL), and heated under reflux for 5 hours. The reaction was cooled to room temperature, and hexane (6 mL) was added. The precipitated solids were filtered, dried by suction to obtain ruthenium complex 1b (288 mg, 90% yield).

$^1$H NMR (400 MHz, CDCl$_3$) δ 3.50-3.39 (m, 1H), 3.31-3.26 (m, 2H), 2.77-2.65 (m, 2H), 2.35-2.09 (m, 6H), 1.86-1.74 (m, 2H), 1.60-1.44 (m, 6H), 1.34-1.08 (m, 18H), −16.30 (t, J=19.2 Hz, 0.12H), −16.54 (t, J=18.0 Hz, 0.88H) ppm; $^{31}$P NMR (161.9 MHz, CDCl$_3$) δ 74.6 (s, br) ppm; HRMS (MALDI) m/z calcd. for C$_{17}$H$_{38}$NOP$_2$$^{96}$Ru: 430.1499. Found: 430.1502 [M-Cl]$^+$; IR (film) 1973, 1960, 1910 cm$^{-1}$.

EXAMPLE 3

Preparation of Catalyst Ruthenium Complex 1c

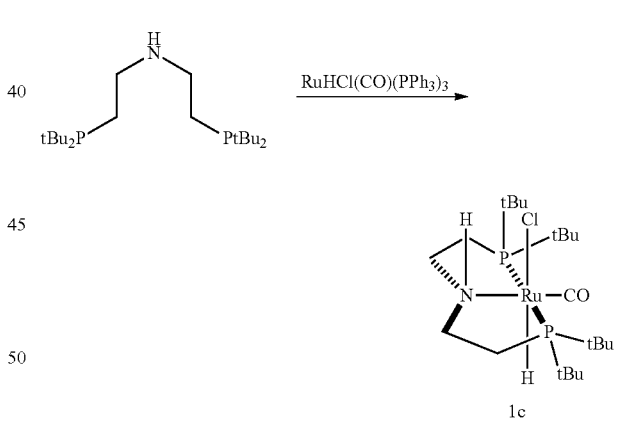

According to the procedure of Example 2, HN(CH$_2$CH$_2$P$^i$Pr$_2$)$_2$ was replaced with HN(CH$_2$CH$_2$PtBu$_2$)$_2$ to obtain ruthenium complex 1c (85% yield).

$^1$H NMR (400 MHz, CDCl$_3$) δ 6.44 (br s, 1H), 3.52-3.37 (m, 0.9H), 3.31-3.19 (m, 2.1H), 3.06-2.91 (m, 2.1H), 2.81-2.69 (m, 0.9H), 2.46-2.14 (m, 4H), 1.77-1.25 (m, 36H), −16.03 (t, J=19.4 Hz, 0.6), −22.32 (t, J=18.4 Hz, 0.4 H) ppm; $^{31}$P NMR (161.9 MHz, CDCl$_3$) δ 89.0 (d, J=9.1 Hz), 87.6 (s) ppm; HRMS (MALDI) m/z calcd. for C$_{21}$H$_{46}$NOP$_2$$^{96}$Ru: 486.2125. Found: 486.2120 [M-Cl]$^+$; IR (film) 1897 cm$^{-1}$.

EXAMPLE 4

Preparation of Catalyst Ruthenium Complex 1d

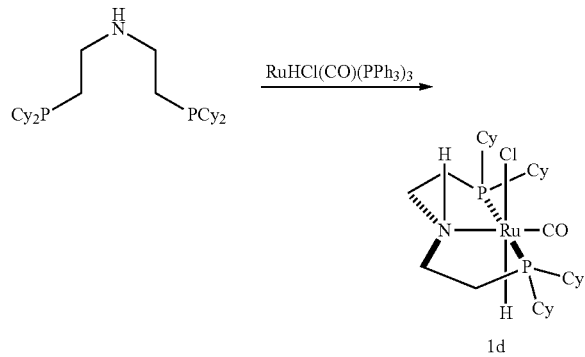

According to the procedure of Example 2, HN(CH$_2$CH$_2$P$^i$Pr$_2$)$_2$ was replaced with HN(CH$_2$CH$_2$PCy$_2$)$_2$ to obtain ruthenium complex 1d (98% yield).

$^1$H NMR (400 MHz, CDCl$_3$) δ 3.85-2.80 (m, 4H), 2.53-1.15 (m, 48H), −16.59 (br s, 1H) ppm; $^{31}$P NMR (161.9 MHz, CDCl$_3$) δ 65.2 (s), 47.6 (s) ppm; HRMS (MALDI) m/z calcd. for C$_{29}$H$_{54}$NOP$_2$$^{96}$Ru: 590.2751. Found: 590.2730 [M-Cl]$^+$; IR (film) 1910 cm$^{-1}$.

EXAMPLE 5

Preparation of Catalyst Ruthenium Complex 1e

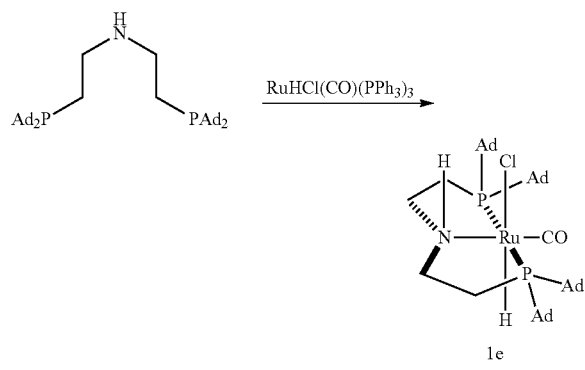

According to the procedure of Example 2, HN(CH$_2$CH$_2$P$^i$Pr$_2$)$_2$ was replaced with HN(CH$_2$CH$_2$PAd$_2$)$_2$ to obtain ruthenium complex 1e (92% yield).

$^1$H NMR (400 MHz, CDCl$_3$) δ 7.49 (br s, 1H), 3.69-3.52 (m, 2H), 2.59-1.60 (m, 66H), −26.05 (t, J=15.6 Hz, 1H) ppm; $^{31}$P NMR (161.9 MHz, CDCl$_3$) δ 84.4 (d, J=9.2 Hz) ppm; HRMS (MALDI) m/z calcd. for C$_{45}$H$_{70}$NOP$_2$$^{96}$Ru: 798.4003. Found: 798.3985 [M-Cl]$^+$; IR (film) 1914 cm$^{-1}$.

EXAMPLE 6

Preparation of Methanol and Ethylene Glycol Through Hydrogenation of Ethylene Carbonate Catalyzed by Ruthenium Complex 1a In a glove box, into a 125 mL autoclave was charged with ruthenium complex 1a (17.4 mg, 0.0286 mmol), potassium tert-butoxide (3.2 mg, 0.0286 mmol), tetrahydrofuran (20 mL), and ethylene carbonate (2.52 g, 28.6 mmol). The autoclave was sealed, removed from the glove box, and filled with hydrogen gas to 50 atm. The reaction vessel was heated in an oil bath at 140° C. with stir for 0.5 hour. The reaction vessel was cooled in an ice-water bath for 1.5 hours, and the excess of hydrogen was slowly deflated. The conversion rate for the reaction was determined as >99% with p-xylene as internal standard by using gas chromatography (using standard curve method; that is, p-xylene is used as internal standard, and standard curve is plotted according to the ratio of the peak area of carbonate, methanol and diol on gas chromatogram to the peak area of xylene, and the amount of carbonate, methanol and diol contained in a reaction system at the end of reaction can be determined by determining the proportion of peak areas in the reaction system). Both of the yields of methanol and ethylene glycol are 99%.

EXAMPLE 7

Preparation of Methanol and Ethylene Glycol Through Hydrogenation of Ethylene Carbonate Catalyzed by Ruthenium Complex 1a In a glove box, into a 125 mL autoclave was charged with a solution of ruthenium complex 1a (1.7 mg, 0.00286 mmol), potassium tert-butoxide (0.32 mg, 0.00286 mmol) in tetrahydrofuran (5 mL), as well as tetrahydrofuran (15 mL) and ethylene carbonate (2.52 g, 28.6 mmol). The autoclave was sealed, removed from the glove box, and filled with hydrogen gas to 50 atm. The reaction vessel was heated in an oil bath at 140° C. with stir for 48 hours. The reaction vessel was cooled in an ice-water bath for 1.5 hours, and the excess of hydrogen was slowly deflated. The conversion rate for the reaction was determined as >99% with p-xylene as internal standard by using gas chromatography. Both of the yields of methanol and ethylene glycol are 99%.

EXAMPLE 8

Preparation of Methanol and Ethylene Glycol Through Hydrogenation of Ethylene Carbonate Catalyzed by Ruthenium Complex 1a In a glove box, into a 125 mL autoclave was charged with a solution of ruthenium complex 1a (0.17 mg, 0.000286 mmol), potassium tert-butoxide (0.032 mg, 0.000286 mmol) in tetrahydrofuran (2 mL), as well as tetrahydrofuran (18 mL) and ethylene carbonate (2.52 g, 28.6 mmol). The autoclave was sealed, removed from the glove box, and filled with hydrogen gas to 60 atm. The reaction vessel was heated in an oil bath at 140° C. with stir for 72 hours. The reaction vessel was cooled in an ice-water bath for 1.5 hours, and the excess of hydrogen was slowly deflated. The conversion rate for the reaction was determined as 89% with p-xylene as internal standard by using gas chromatography. The yields of methanol and ethylene glycol are 84% and 87%, respectively.

EXAMPLE 9

Preparation of Methanol and Ethylene Glycol Through Hydrogenation of Ethylene Carbonate Catalyzed by Ruthenium Complex 1b In a glove box, into a 125 mL autoclave was charged with ruthenium complex 1b (13.5 mg, 0.0286 mmol), potassium tert-butoxide (3.2 mg, 0.0286 mmol), tetrahydrofuran (20 mL) and ethylene carbonate (2.52 g, 28.6 mmol). The autoclave was sealed, removed from the glove box, and filled with hydrogen gas to 50 atm. The reaction vessel was heated in an oil bath at 140° C. with stir for 0.5 hour. The reaction vessel was cooled in an ice-water bath for 1.5 hours, and the excess of hydrogen was slowly deflated. The conversion rate for the reaction was determined as 74% with p-xylene as internal standard by using gas chromatography. The yields of methanol and ethylene glycol are 45% and 74%, respectively.

EXAMPLE 10

Preparation of Methanol and Ethylene Glycol Through Hydrogenation of Ethylene Carbonate Catalyzed by Ruthenium Complex 1d In a glove box, into a 125 mL autoclave was charged with ruthenium complex 1d (18.0 mg, 0.0286 mmol), potassium tert-butoxide (3.2 mg, 0.0286 mmol), tetrahydrofuran (20 mL) and ethylene carbonate (2.52 g, 28.6 mmol). The autoclave was sealed, removed from the glove box, and filled with hydrogen gas to 50 atm. The reaction vessel was heated in an oil bath at 140° C. with stir for 0.5 hour. The reaction vessel was cooled in an ice-water bath for 1.5 hours, and the excess of hydrogen was slowly deflated. The conversion rate for the reaction was determined as 76% with p-xylene as internal standard by using gas chromatography. The yields of methanol and ethylene glycol are 48% and 76%, respectively.

EXAMPLE 11

Hydrogenation of Propylene Carbonate Catalyzed by Ruthenium Complex 1a

In a glove box, into a 125 mL autoclave was charged with ruthenium complex 1a (3.5 mg, 0.057 mmol), potassium tert-butoxide (0.5 mg, 0.057 mmol), tetrahydrofuran (20 mL) and propylene carbonate (2.92 g, 28.6 mmol). The autoclave was sealed, removed from the glove box, and filled with hydrogen gas to 50 atm. The reaction vessel was heated in an oil bath at 140° C. with stir for 10 hours. The reaction vessel was cooled in an ice-water bath for 1.5 hours, and the excess of hydrogen was slowly deflated. The conversion rate for the reaction was determined as 99% with p-xylene as internal standard by using gas chromatography. Both of the yields of methanol and ethylene glycol are 99%.

EXAMPLE 12

Hydrogenation of Cyclic Carbonate, 4-ethyl-1,3-dioxan-2-one Catalyzed by Ruthenium Complex 1a In a glove box, into a 125 mL autoclave was charged with ruthenium complex 1a (8.7 mg, 0.0143 mmol), potassium tert-butoxide (1.6 mg, 0.0143 mmol), tetrahydrofuran (20 mL) and 4-ethyl-1,3-dioxan-2-one (3.32 g, 28.6 mmol). The autoclave was sealed, removed from the glove box, and filled with hydrogen gas to 50 atm. The reaction vessel was heated in an oil bath at 140° C. with stir for 10 hours. The reaction vessel was cooled in an ice-water bath for 1.5 hours, and the excess of hydrogen was slowly deflated. The conversion rate for the reaction was determined as >99% with p-xylene as internal standard by using gas chromatography. The yields of methanol and ethylene glycol are 99% and 96%, respectively.

EXAMPLE 13

Hydrogenation of Cyclic Carbonate, 4-butyl-1,3-dioxan-2-one Catalyzed by Ruthenium Complex 1a In a glove box, into a 125 mL autoclave was charged with ruthenium complex 1a (8.7 mg, 0.0143 mmol), potassium tert-butoxide (1.6 mg, 0.0143 mmol), tetrahydrofuran (20 mL) and 4-butyl-1,3-dioxan-2-one (4.12 g, 28.6 mmol). The autoclave was sealed, removed from the glove box, and filled with hydrogen gas to 50 atm. The reaction vessel was heated in an oil bath at 140° C. with stir for 4 hours. The reaction vessel was cooled in an ice-water bath for 1.5 hours, and the excess of hydrogen was slowly deflated. The yield of methanol was determined as 99% with p-xylene as internal standard by using gas chromatography. The separation yield of the diol is 99%.

EXAMPLE 14

Hydrogenation of Cyclic Carbonate, 4-phenyl-1,3-dioxan-2-one Catalyzed by Ruthenium Complex 1a In a glove box, into a 125 mL autoclave was charged with ruthenium complex 1a (8.7 mg, 0.0143 mmol), potassium tert-butoxide (1.6 mg, 0.0143 mmol), tetrahydrofuran (20 mL) and 4-phenyl-1,3-dioxan-2-one (4.69 g, 28.6 mmol). The autoclave was sealed, removed from the glove box, and filled with hydrogen gas to 50 atm. The reaction vessel was heated in an oil bath at 140° C. with stir for 4 hours. The reaction vessel was cooled in an ice-water bath for 1.5 hours, and the excess of hydrogen was slowly deflated. The yield of methanol was determined as 99% with p-xylene as internal standard by using gas chromatography. The separation yield of the diol is 99%.

EXAMPLE 15

Hydrogenation of Cyclic Carbonate, 4-benzyl-1,3-dioxan-2-one Catalyzed by Ruthenium Complex 1a In a glove box, into a 125 mL autoclave was charged with ruthenium complex 1a (8.7 mg, 0.0143 mmol), potassium tert-butoxide (1.6 mg, 0.0143 mmol), tetrahydrofuran (20 mL) and 4-benzyl-1,3-dioxan-2-one (5.09 g, 28.6 mmol). The autoclave was sealed, removed from the glove box, and filled with hydrogen gas to 50 atm. The reaction vessel was heated in an oil bath at 140° C. with stir for 4 hours. The reaction vessel was cooled in an ice-water bath for 1.5 hours, and the excess of hydrogen was slowly deflated. The yield of methanol was determined as 99% with p-xylene as internal standard by using gas chromatography. The separation yield of the diol is 98%.

EXAMPLE 16

Hydrogenation of Cyclic Carbonate, 4-methoxymethyl-1,3-dioxan-2-one Catalyzed by Ruthenium Complex 1a In a glove box, into a 125 mL autoclave was charged with ruthenium complex 1a (8.7 mg, 0.0143 mmol), potassium tert-butoxide (1.6 mg, 0.0143 mmol), tetrahydrofuran (20 mL) and 4-methoxymethyl-1,3-dioxan-2-one (3.78 g, 28.6 mmol). The autoclave was sealed, removed from the glove box, and filled with hydrogen gas to 50 atm. The reaction vessel was heated in an oil bath at 140° C. with stir for 4 hours. The reaction vessel was cooled in an ice-water bath for 1.5 hours, and the excess of hydrogen was slowly deflated. The yield of methanol was determined as 99% with p-xylene as internal standard by using gas chromatography. The separation yield of the diol is 99%.

EXAMPLE 17

Hydrogenation of Cyclic Carbonate, 4-benzyloxymethyl-1,3-dioxan-2-one Catalyzed by Ruthenium Complex 1a In a glove box, into a 125 mL autoclave was charged with ruthenium complex 1a (8.7 mg, 0.0143 mmol), potassium tert-butoxide (1.6 mg, 0.0143 mmol), tetrahydrofuran (20 mL) and 4-benzyloxymethyl-1,3-dioxan-2-one (5.94 g, 28.6 mmol). The autoclave was sealed, removed from the glove box, and filled with hydrogen gas to 50 atm. The reaction vessel was heated in an oil bath at 140° C. with stir for 4 hours. The reaction vessel was cooled in an ice-water bath for 1.5 hours, and the excess of hydrogen was slowly deflated. The yield of methanol was determined as 99% with p-xylene as internal standard by using gas chromatography. The separation yield of the diol is 97%.

EXAMPLE 18

Hydrogenation of Cyclic Carbonate, 4,5-dimethyl-1,3-dioxan-2-one Catalyzed by Ruthenium Complex 1a In a glove box, into a 125 mL autoclave was charged with ruthenium complex 1a (8.7 mg, 0.0143 mmol), potassium tert-butoxide (1.6 mg, 0.0143 mmol), tetrahydrofuran (20 mL) and 4,5-dimethyl-1,3-dioxan-2-one (3.32 g, 28.6 mmol). The autoclave was sealed, removed from the glove box, and filled with hydrogen gas to 50 atm. The reaction vessel was heated in an oil bath at 140° C. with stir for 10 hours. The reaction vessel was cooled in an ice-water bath for 1.5 hours, and the excess of hydrogen was slowly deflated. The yield of methanol was determined as 99% with p-xylene as internal standard by using gas chromatography. The separation yield of the diol is 98%.

EXAMPLE 19

Hydrogenation of Cyclic Carbonate, 4,4-dimethyl-1,3-dioxan-2-one Catalyzed by Ruthenium Complex 1a In a glove box, into a 125 mL autoclave was charged with ruthenium complex 1a (8.7 mg, 0.0143 mmol), potassium tert-butoxide (1.6 mg, 0.0143 mmol), tetrahydrofuran (20 mL) and 4,4-dimethyl-1,3-dioxan-2-one (3.32 g, 28.6 mmol). The autoclave was sealed, removed from the glove box, and filled with hydrogen gas to 50 atm. The reaction vessel was heated in an oil bath at 140° C. with stir for 12 hours. The reaction vessel was cooled in an ice-water bath for 1.5 hours, and the excess of hydrogen was slowly deflated. The yield of methanol was determined as 99% with p-xylene as internal standard by using gas chromatography. The separation yield of the diol is 97%.

EXAMPLE 20

Hydrogenation of Cyclic Carbonate, 4,4,5,5-tetramethyl-1,3-dioxan-2-one Catalyzed by Ruthenium Complex 1a In a glove box, into a 125 mL autoclave was charged with ruthenium complex 1a (17.4 mg, 0.0286 mmol), potassium tert-butoxide (3.2 mg, 0.0286 mmol), tetrahydrofuran (20 mL) and 4,4,5,5-tetramethyl-1,3-dioxan-2-one (4.12 g, 28.6 mmol). The autoclave was sealed, removed from the glove box, and filled with hydrogen gas to 50 atm. The reaction vessel was heated in an oil bath at 140° C. with stir for 20 hours. The reaction vessel was cooled in an ice-water bath for 1.5 hours, and the excess of hydrogen was slowly deflated. The yield of methanol was determined as 95% with p-xylene as internal standard by using gas chromatography. The separation yield of the diol is 96%.

EXAMPLE 21

Hydrogenation of Cyclic Carbonate, 1,3-dioxan-2-one Catalyzed by Ruthenium Complex 1a In a glove box, into a 125 mL autoclave was charged with ruthenium complex 1a (8.7 mg, 0.0143 mmol), potassium tert-butoxide (1.6 mg, 0.0143 mmol), tetrahydrofuran (20 mL) and 1,3-dioxan-2-one (2.92 g, 28.6 mmol). The autoclave was sealed, removed from the glove box, and filled with hydrogen gas to 50 atm. The reaction vessel was heated in an oil bath at 140° C. with stir for 2 hours. The reaction vessel was cooled in an ice-water bath for 1.5 hours, and the excess of hydrogen was slowly deflated. The conversion rate for the reaction was determined as >99% with p-xylene as internal standard by using gas chromatography. The yields of methanol and diol are 99% and 99%, respectively.

EXAMPLE 22

Degradation of Poly(Propylene Carbonate) Through Hydrogenation Catalyzed by Ruthenium Complex 1a In a glove box, into a 125 mL autoclave was charged with ruthenium complex 1a (15.8 mg, 0.0260 mmol), potassium tert-butoxide (2.9 mg, 0.0260 mmol), tetrahydrofuran (25 mL) and poly(propylene carbonate) [$M_w$=100,698 ($M_w$/$M_n$=1.77), >99% carbonate linkage] (2.69 g, 26.0 mmol). The autoclave was sealed, removed from the glove box, and filled with hydrogen gas to 50 atm. The reaction vessel was heated in an oil bath at 140° C. with stir for 24 hours. The reaction vessel was cooled in an ice-water bath for 1.5 hours, and the excess of hydrogen was slowly deflated. The conversion rate for the reaction was determined as >99% with p-xylene as internal standard by using gas chromatography. The yields of methanol and the diol are 99% and 99%, respectively.

EXAMPLE 23

Preparation of Deuterated Methanol and Deuterated Ethylene Glycol Through Deuteration of Ethylene Carbonate Catalyzed by Ruthenium Complex 1a In a glove box, into a 125 mL autoclave was charged with ruthenium complex 1a (17.4 mg, 0.0286 mmol), potassium tert-butoxide (3.2 mg, 0.0286 mmol), tetrahydrofuran (20 mL) and ethylene carbonate (2.52 g, 28.6 mmol). The autoclave was sealed, removed from the glove box, and filled with deuterium gas to 50 atm. The reaction vessel was heated in an oil bath at 140° C. with stir for 0.5 hour. The reaction vessel was cooled in an ice-water bath for 1.5 hours, and the excess of hydrogen was slowly deflated. The conversion rate for the reaction was determined as >99% with p-xylene as internal standard by using gas chromatography. The yield of methanol is 99%, and the content of deuterium atom on methyl is 87% (determined by converting methanol into methyl benzoate and then performing NMR method).

EXAMPLE 24

Preparation of Deuterated Methanol Through Deuteration of Tetramethyl Ethylene Carbonate Catalyzed by Ruthenium Complex 1a In a glove box, into a 125 mL autoclave was charged with ruthenium complex 1a (17.4 mg, 0.0286 mmol), potassium tert-butoxide (3.2 mg, 0.0286 mmol), tetrahydrofuran (20 mL) and 4,4,5,5-tetramethyl-1,3-dioxan-2-one (4.12 g, 28.6 mmol). The autoclave was sealed, removed from the glove box, and filled with deuterium gas to 50 atm. The reaction vessel was heated in an oil bath at 140° C. with stir for 24 hours. The reaction vessel was cooled in an ice-water bath for 1.5 hours, and the excess of hydrogen was slowly deflated. The conversion rate for the reaction was determined as >99% with p-xylene as internal standard by using gas chromatography. The yield of methanol is 99%, and the content of deuterium atom on methyl is >99% (determined by converting methanol into methyl benzoate and then performing NMR method).

EXAMPLE 25

Preparation of Methanol and Ethylene Glycol Through Hydrogenation of Ethylene Carbonate Catalyzed by Ruthenium Complexes 1c and 1e The process in Example 6 was used, except that ruthenium complexes 1c and 1e were used to catalyze the hydrogenation of ethylene carbonate for preparing methanol and ethylene glycol. Determined by the same gas chromatography as those in the above Examples, comparable conversion rate and yield were obtained by preparing methanol and ethylene glycol through hydrogenation of ethylene carbonate catalyzed by ruthenium complexes 1c and 1e.

EXAMPLE 26

Preparation of Methanol Through Hydrogenation of Dimethyl Carbonate Catalyzed by Ruthenium Complex 1a In a glove box, into a 125 mL autoclave was charged with ruthenium complex 1a (17.4 mg, 0.0286 mmol), potassium tert-butoxide (3.2 mg, 0.0286 mmol), tetrahydrofuran (10 mL) and dimethyl carbonate (2.57 g, 28.6 mmol). The autoclave was sealed, removed from the glove box, and filled with hydrogen gas to 50 atm. The reaction vessel was heated in an oil bath at 140° C. with stir for 10 hours. The reaction vessel was cooled in an ice-water bath for 1.5 hours, and the excess of hydrogen was slowly deflated. The conversion rate of dimethyl carbonate was determined as 95% with p-xylene as internal standard by using gas chromatography. The yield of methanol is 94%.

EXAMPLE 27

Hydrogenation of Propylene Carbonate Catalyzed by Complex 1a' Formed from Ruthenium and [P(N-Me)P] Pincer-Like Ligand The ruthenium complex of formula 1a' was prepared by using a procedure similar to those of Examples 1-5:

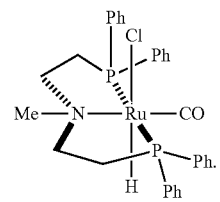

1a'

RuHCl(CO)[(Ph$_2$PCH$_2$CH$_2$)$_2$NMe] (1a'): yield 98%, pale yellow solid. $^1$H NMR (400 MHz, CDCl$_3$) δ 7.90-7.65 (m, 8H), 7.48-6.79 (m, 12H), 4.01-3.90 (m, 0.6H), 3.21-2.72 (m, 7.4H), 2.53 (s, 2H), 2.35 (s, 1H), −14.16 (t, J=19.6 Hz, 0.3H), −14.75 (t, J=19.6 Hz, 0.7H) ppm; $^{31}$P NMR (161.9 MHz, CDCl$_3$) δ 54.4 (s), 49.5 (d, J=6.3 Hz) ppm; HRMS (MALDI) m/z calcd. for [C$_{30}$H$_{30}$NOP$_2$$^{96}$Ru]$^+$: 578.0873. Found: 578.0863 [M-H$_2$—Cl]$^+$; IR (film) 1975, 1903 cm$^{-1}$.

A procedure similar to that of Example 11 was used to catalyze the hydrogenation of propylene carbonate by using the ruthenium complex of formula 1a'. Neither of methanol and propylene glycol was produced, therefore, the ruthenium complex of formula 1a' did not have activity.

From formula 1a', it is obvious that the structure shown in 1a' is similar to the ruthenium complex of formula 1a, and the only difference is that, in formula 1a, H is connected to N, while in formula 1a', H is connected to methyl. Therefore, the conclusion of this embodiment will further demonstrate the following consensus in the field of metal catalyst that: different catalytic activities of metal complexes may be resulted from different ligands with different structures.

EXAMPLE 28

Effects of Different Amounts of Base on the Hydrogenation of Propylene Carbonate Catalyzed by Ruthenium Complexes 1a At 100° C., under different mole ratios of base to ruthenium complex and the following conditions, catalytic hydrogenation of propylene carbonate was performed for 2 hrs using a procedure similar to that of Example 11 and ruthenium complex 1a as catalyst:

| No. | KOtBu[x] | Conversion rate [%] | Yield of diol [%] | Yield of methanol [%] |
|---|---|---|---|---|
| 1 | 0 | 0 | 0 | 0 |
| 2 | 0.5 | 27 | 26 | 26 |
| 3 | 1 | 81 | 79 | 79 |
| 4 | 1.5 | 75 | 73 | 75 |
| 5 | 2 | 71 | 66 | 69 |
| 6 | 3 | 42 | 40 | 40 |
| 7 | 6 | 48 | 46 | 46 |
| 8 | 10 | 37 | 37 | 36 |
| 9 | 20 | 30 | 28 | 28 |

In the above table: propylene carbonate: 28.6 mmol; and the conversion rate of propylene carbonate, the yields of diol and methanol were determined by gas chromatography with p-xylene as internal standard.

From the results shown in the above Table, it will be known that, in the absence of a base, no reaction will occur by merely using ruthenium complex 1a. The amount of a base will have certain effects on the reaction; and preferably, the best effects will be produced when the molar ratio of base to ruthenium complex is 1-2:1.

EXAMPLE 29

Hydrogenation of Propylene Carbonate in Toluene Catalyzed by Ruthenium Complex 1a In a glove box, into a 125 mL autoclave was charged with ruthenium complex 1a (1.8 mg, 0.028 mmol), potassium tert-butoxide (0.25 mg, 0.028 mmol), toluene (20 mL) and propylene carbonate (2.92 g, 28.6 mmol). The autoclave was sealed, removed from the glove box, and filled with hydrogen gas to 50 atm. The reaction vessel was heated in an oil bath at 100° C. with stir for 10 hours. The reaction vessel was cooled in an ice-water bath for 1.5 hours, and the excess of hydrogen was slowly deflated. The conversion rate of the raw material was determined as 99% with p-xylene as internal standard by using gas chromatography. Both of the yields of methanol and diol are 99%.

EXAMPLE 30

Hydrogenation of Propylene Carbonate in Dioxane Catalyzed by Ruthenium Complex 1a In a glove box, into a 125 mL autoclave was charged with ruthenium complex 1a (1.8 mg, 0.028 mmol), potassium tert-butoxide (0.25 mg, 0.028 mmol), dioxane (20 mL) and propylene carbonate (2.92 g, 28.6 mmol). The autoclave was sealed, removed from the glove box, and filled with hydrogen gas to 50 atm. The reaction vessel was heated in an oil bath at 100° C. with stir for 10 hours. The reaction vessel was cooled in an ice-water bath for 1.5 hours, and the excess of hydrogen was slowly deflated. The conversion rate of the raw material was determined as 99% with p-xylene as internal standard by using gas chromatography. Both of the yields of methanol and diol are 99%.

EXAMPLE 31

Hydrogenation of Propylene Carbonate Catalyzed by Ruthenium Complexes 1a at Different Temperatures At different reaction temperatures, catalytic hydrogenation of propylene carbonate was performed using a procedure similar to that of Example 11 and ruthenium complex 1a as catalyst, and the results are shown in the following Table:

| No. | Temperature (° C.) | Time [hr] | Conversion rate [%] | Yield of diol [%] | Yield of methanol [%] |
|---|---|---|---|---|---|
| 1 | 80 | 72 | >99 | 99 | 99 |
| 2 | 100 | 10 | >99 | 99 | 99 |
| 3 | 120 | 6 | >99 | 98 | 98 |
| 4 | 140 | 2 | >99 | 99 | 99 |

In the above table: propylene carbonate: 28.6 mmol; and the conversion rate of propylene carbonate, the yields of diol and methanol were determined by gas chromatography with p-xylene as internal standard.

From the results shown in the above Table, it will be known that the time needed for complete conversion of propylene carbonate will be varied with different reaction temperatures. At a higher temperature, the reactants will be completely converted in a shorter time.

EXAMPLE 32

Hydrogenation of Propylene Carbonate Catalyzed by Ruthenium Complexes 1a at Different Hydrogen Pressures At 100° C., under different hydrogen pressures, catalytic hydrogenation of propylene carbonate was performed for 2 hrs using a procedure similar to that of Example 11 and ruthenium complex 1a as catalyst, and the results are shown in the following Table:

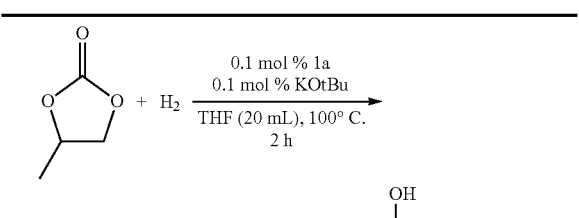

| No. | H₂ pressure (atm) | Conversion rate [%] | Yield of diol [%] | Yield of methanol [%] |
| --- | --- | --- | --- | --- |
| 1 | 50 | 81 | 79 | 79 |
| 2 | 30 | 50 | 48 | 47 |
| 3 | 20 | 41 | 40 | 38 |
| 4 | 10 | 26 | 25 | 24 |

In the above table: propylene carbonate: 28.6 mmol; and the conversion rate of propylene carbonate, the yields of diol and methanol were determined by gas chromatography with p-xylene as internal standard.

From the results shown in the above Table, it will be known that, within the same reaction time, improving the hydrogen pressure will be helpful to accelerate the hydrogenation of propylene carbonate catalyzed by ruthenium complexes 1a with other reaction conditions fixed.

EXAMPLE 33

Preparation of Methanol and Phenol Through Hydrogenation of Diphenyl Carbonate Catalyzed by Ruthenium Complexes 1a In a glove box, into a 125 mL autoclave was charged with ruthenium complex 1a (17.4 mg, 0.0286 mmol), potassium tert-butoxide (3.2 mg, 0.0286 mmol), tetrahydrofuran (10 mL) and diphenyl carbonate (0.61 g, 2.86 mmol). The autoclave was sealed, removed from the glove box, and filled with hydrogen gas to 50 atm. The reaction vessel was heated in an oil bath at 140° C. with stir for 10 hours. The reaction vessel was cooled in an ice-water bath for 1.5 hours, and the excess of hydrogen was slowly deflated. The conversion rate of diphenyl carbonate was determined as 100% with p-xylene as internal standard by using gas chromatography. The yield of methanol is 95%, and the yield of phenol is 99%.

Therefore, this example demonstrated that the system can also effectively catalyze the hydrogenation of diester formed from carbonic acid and phenols, so as to obtain methanol and corresponding phenols.

EXAMPLE 34

Hydrogenation of Propylene Carbonate Catalyzed by Ruthenium Complexes 1a Under Neutral Condition Under an inert gas atmosphere, ruthenium complex 1a (17.4 mg, 0.0286 mmol) and potassium tert-butoxide (3.2 mg, 0.0286 mmol) were mixed in tetrahydrofuran (10 mL) and stirred for 30 minutes at room temperature. The solvent was removed by suction under reduced pressure. Benzene (20 mL) was added, stirred for 10 minutes at room temperature and filtered. The filtrate was dried by suction to give the newly prepared ruthenium complex. In a glove box, into a 125 mL autoclave was charged with such neutral ruthenium complex, tetrahydrofuran (20 mL) and propylene carbonate (2.92 g, 28.6 mmol). The autoclave was sealed, removed from the glove box, and filled with hydrogen gas to 50 atm. The reaction vessel was heated in an oil bath at 140° C. with stir for 10 hours. The reaction vessel was cooled in an ice-water bath for 1.5 hours, and the excess of hydrogen was slowly deflated. The conversion rate of the reaction was determined as 99% with p-xylene as internal standard by using gas chromatography. Both of the yields of methanol and diol are 99%.

Therefore, this example demonstrates that the hydrogenation of the cyclic carbonate can be effectively catalyzed by a suitable ruthenium complex under neutral conditions, so as to obtain methanol and the corresponding diol.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for preparing methanol and diol, wherein said method comprises, under hydrogen atmosphere, subjecting a cyclic carbonate or polycarbonate to the following reaction under the action of a catalyst, so as to give methanol and diol,

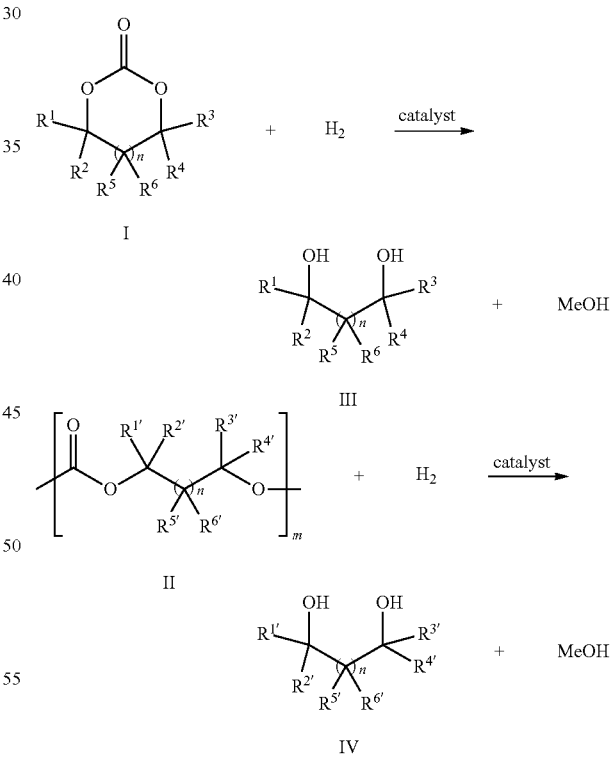

in formula I and III:

n=0~20, m=2~1000000;

$R^1, R^2, R^3, R^4, R^5, R^6$ can be independently selected from a hydrogen, a $C_1~C_{20}$ alkyl, a $C_4~C_{24}$ aryl, a $C_5~C_{25}$ aryl alkyl, —($C_1~C_8$)—$OR^7$, —($C_1~C_8$)—$SR^8$, or —($C_1~C_8$)—$NR^9R^{10}$;

$R^5, R^6$ may be further independently selected from a $C_4~C_{10}$ cycloalkyl;

wherein $R^7$, $R^8$, $R^9$, $R^{10}$ are independently selected from a $C_1$~$C_{10}$ alkyl, a $C_4$~$C_{24}$ aryl or a $C_5$~$C_{25}$ aryl alkyl, and $R^9$, $R^{10}$ may also be joined atom to form a cyclic amine group with the nitrogen;

when n=0, $R^1$ and $R^3$ may be joined to form an alicyclic group or aryl ring;

when n≥1, $R^1$ and $R^5$, $R^3$ and $R^6$ may be joined to form an alicyclic group or an aryl ring;

in formula II and IV:

$R^{1'}$, $R^{2'}$, $R^{3'}$, $R^{4'}$, $R^{5'}$, $R^{6'}$ may be independently selected from a hydrogen, a $C_1$~$C_{20}$ alkyl, a $C_4$~$C_{24}$ aryl, a $C_5$~$C_{25}$ aryl alkyl, —($C_1$~$C_8$)—$OR^{7'}$, —($C_1$~$C_8$)—$SR^{8'}$ or —($C_1$~$C_8$)—$NR^{9'}R^{10'}$;

$R^{5'}$, $R^{6'}$ may be further independently selected from a $C_4$~$C_{10}$ cycloalkyl;

wherein $R^{7'}$, $R^{8'}$, $R^{9'}$, $R^{10'}$ are independently selected from a $C_1$~$C_{10}$ alkyl, a $C_4$~$C_{24}$ aryl or a $C_5$~$C_{25}$ aryl alkyl, $R^{9'}$, $R^{10'}$ may be further joined to form a cyclic amine group with the nitrogen atom;

when n=0, $R^{1'}$ and $R^{3'}$ may be joined to form an alicyclic group or aryl ring;

when n≥1, $R^{1'}$ and $R^{5'}$, $R^{3'}$ and $R^{6'}$ may be joined to form an alicyclic group or an aryl ring.

2. The method according to claim 1, wherein the catalyst is a compound of transition metal of Group VIIIB.

3. The method according to claim 2, wherein the transition metal of Group VIIIB is selected from Fe, Co, Ni, Ru, Rh, Pd, Os, Ir or Pt.

4. The method according to any one of claims 1-3, wherein the method includes conducting the following reaction in the presence of an organic solvent and a base:

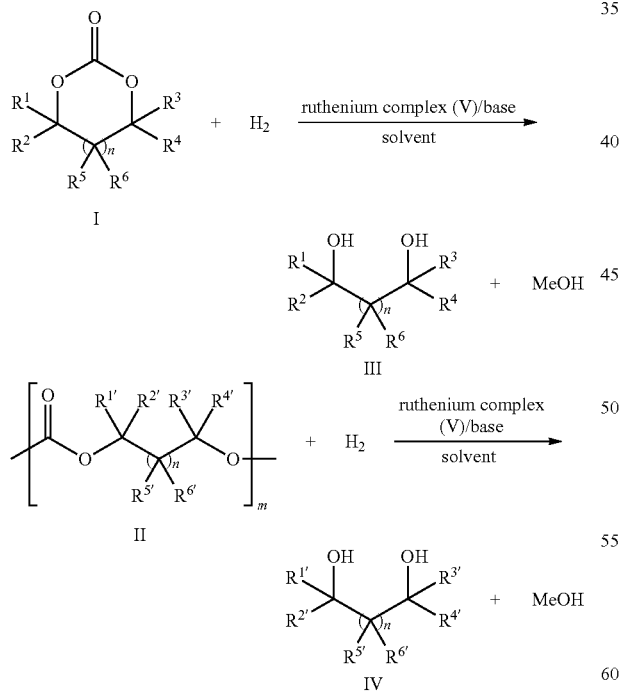

wherein the compounds of structural formula I, II, III and IV are defined as in claim 1, and the ruthenium complex V has the general structural formula V:

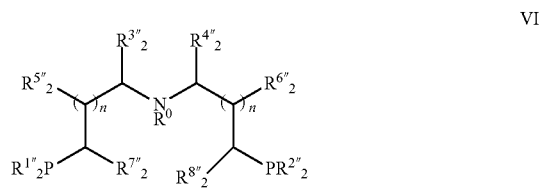

in formula V:

X is carbon monoxide, triphenylphosphine, pyridine, tetrahydrofuran or dimethyl sulfoxide;

Y, Y' are independently selected from: a hydride ion, a hydroxyl ion, a chloride ion, a bromide ion, an iodide ion and $BH_4^-$, $BH_3CN^-$, $BH(Et)_3^-$, $BH(sec-Bu)_3^-$, $AlH_4^-$ or $AlH_2(OCH_2CH_2CH_3)_2^-$;

wherein L is a tridentate amino bisphosphorus ligand of general structural formula VI:

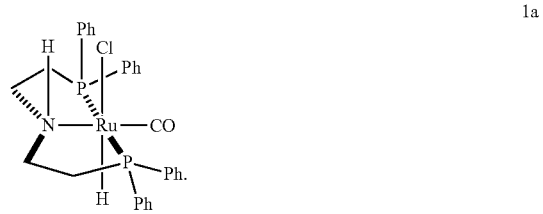

in general formula VI, n=0~3;

$R^0$ is H;

$R^{1''}$, $R^{2''}$ are independently selected from a $C_1$~$C_{10}$ alkyl, a $C_3$~$C_{10}$ cycloalkyl, a $C_4$~$C_{24}$ aryl or an adamantyl, wherein the aryl includes an unsubstituted or substituted aryl;

$R^{3''}$, $R^{4''}$, $R^{5''}$, $R^{6''}$, $R^{7''}$, $R^{8''}$ are independently selected from a hydrogen, a $C_1$~$C_{10}$ alkyl, a $C_3$~$C_{10}$ cycloalkyl, a $C_1$~$C_{10}$ alkoxy or a $C_4$~$C_{36}$ aryl;

when n=0, $R^{3''}$ and $R^{7''}$, $R^{4''}$ and $R^{8''}$ may be joined to form an alicyclic group or an aryl ring;

when n≥1, $R^{3''}$ and $R^{5''}$, $R^{4''}$ and $R^{6''}$, $R^{5''}$ and $R^{7''}$ as well as $R^{6''}$ and $R^{8''}$ may be joined to form an alicyclic group or an aryl ring.

5. The method according to claim 4, wherein the ruthenium complex V is shown in structural formula 1a:

6. The method according to claim 4, wherein the molar ratio of the cyclic carbonate or polycarbonate to ruthenium complex is 100~1000000:1.

7. The method according to claim 4, wherein the base is an alkali metal salt of alcohol, an alkali metal carbonate, or an alkali metal hydroxide.

8. The method according to claim 4, wherein the molar ratio of base to ruthenium complex is 1 to 100:1.

9. The method according to claim 4, wherein the temperature for the reaction is 60-180° C.

10. The method according to claim 4, wherein the reaction time for the reaction is 0.1-1000 hours.

11. The method according to claim 4, wherein the hydrogen pressure for the reaction is 1-100 atmospheres.

12. A ruthenium complex according to structural formula 1b-1e:

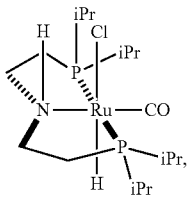

1b

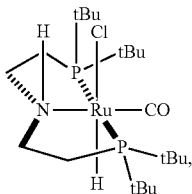

1c

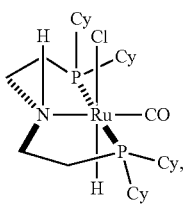

1d

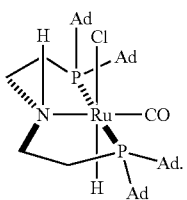

1e

13. A method for preparing deuterated methanol and deuterated diol, wherein the method includes performing the method according to any one of claims 1-11 by using deuterium $D_2$ instead of hydrogen $H_2$, so as to give deuterated methanol and deuterated diol.

14. A method for preparing alcohol, wherein the method includes, in the presence of a ruthenium complex (V) and a base, reducing carbonate through hydrogenation in a organic solvent, so as to give alcohol, wherein the ruthenium complex is shown in formula V $$Ru(L)XYY' \qquad (V);$$

in formula V:

X is carbon monoxide, triphenylphosphine, pyridine, tetrahydrofuran or dimethyl sulfoxide;

Y, Y' are independently selected from: a hydride ion, a hydroxyl ion, a chloride ion, a bromide ion, an iodide ion and $BH_4^-$, $BH_3CN^-$, $BH(Et)_3^-$, $BH(sec-Bu)_3^-$, $AlH_4^-$ or $AlH_2(OCH_2CH_2CH_3)_2^-$;

wherein L is a tridentate amino bisphosphorus ligand of general structural formula VI:

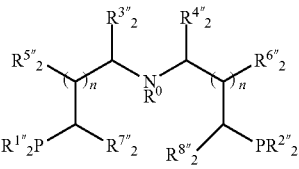

VI in general formula VI, n=0~3;

$R^0$ is H;

$R^{1''}$, $R^{2''}$ are independently selected from a $C_1$~$C_{10}$ alkyl, a $C_3$~$C_{10}$ cycloalkyl, a $C_4$~$C_{24}$ aryl or an adamantyl, wherein the aryl is an unsubstituted or substituted aryl;

$R^{3''}$, $R^{4''}$, $R^{5''}$, $R^{6''}$, $R^{7''}$, $R^{8''}$ are independently selected from a hydrogen, a $C_1$~$C_{10}$ alkyl, a $C_3$~$C_{10}$ cycloalkyl, a $C_1$~$C_{10}$ alkoxy or a $C_4$~$C_{36}$ aryl;

when n=0, $R^{3''}$ and $R^{7''}$, $R^{4''}$ and $R^{8''}$ may be joined to form an alicyclic group or an aryl ring;

when n≥1, $R^{3''}$ and $R^{5''}$, $R^{4''}$ and $R^{6''}$, $R^{5''}$ and $R^{7''}$ as well as $R^{6''}$ and $R^{8''}$ may be joined to form an alicyclic group or an aryl ring.

* * * * *